US00PP36824P2

(12) United States Plant Patent
Nir

(10) Patent No.: US PP36,824 P2
(45) Date of Patent: Jul. 15, 2025

(54) ***CHAMELAUCIUM* PLANT NAMED 'DUAL STAR'**

(50) Latin Name: *Chamelaucium uncinatum*
Varietal Denomination: DUAL STAR

(71) Applicant: Nitzan Nir, Kfar Hess (IL)

(72) Inventor: Nitzan Nir, Kfar Hess (IL)

( * ) Notice: Subject to any disclaimer, the term of this patent is extended or adjusted under 35 U.S.C. 154(b) by 0 days.

(21) Appl. No.: 18/889,484

(22) Filed: Sep. 19, 2024

(51) Int. Cl.
*A01H 6/00* (2018.01)
*A01H 5/02* (2018.01)

(52) U.S. Cl.
USPC ..... Plt./229

(58) Field of Classification Search
USPC ..... Plt./229
CPC ..... A01H 6/00; A01H 5/02
See application file for complete search history.

*Primary Examiner* — Keith O. Robinson
(74) *Attorney, Agent, or Firm* — Cassandra Bright

(57) ABSTRACT

A new and distinct cultivar of *Chamelaucium* plant named 'DUAL STAR' is disclosed, characterized by a plant producing abundant large pink and white flowers in winter. Plants have distinctively long internodes. The new variety is a *Chamelaucium*, normally used for cut flower stem production, or as a garden or container plant.

2 Drawing Sheets

Figure 1:
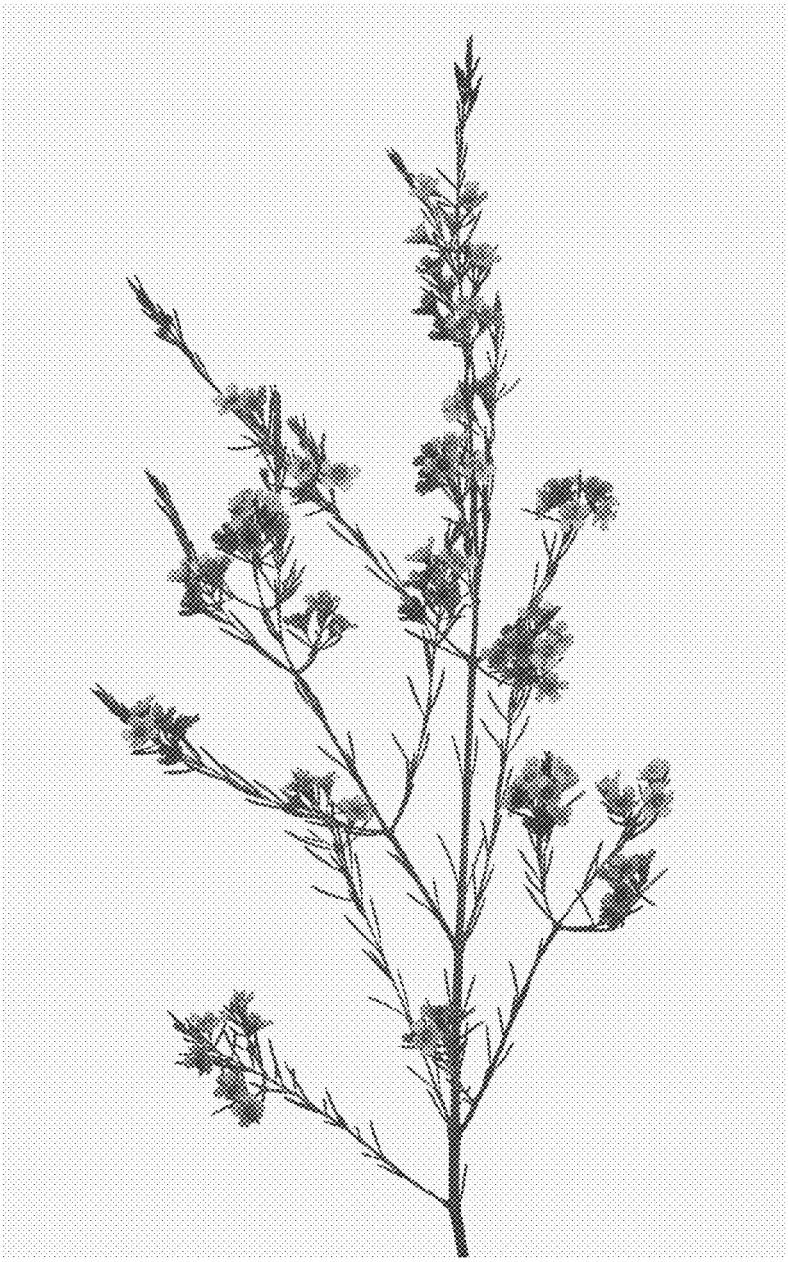

Latin name of the genus and species: *Chamelaucium uncinatum.*

Variety denomination: 'DUAL STAR'.

BACKGROUND OF THE INVENTION

The new *Chamelaucium* cultivar is the product of a planned breeding program conducted by the inventor, Nitzan Nir, in Kfar Hess, Israel. The objective of the breeding program was to produce new *Chamelaucium* varieties for ornamental commercial applications. The new variety was selected as a seedling from the breeding program at a commercial nursery in Kfar Hess, Israel.

The crossing resulting in this new variety was made in March of 2017. The seed parent is the unpatented variety referred to as *Chamelaucium uncinatum* 'Sweet 16'. The pollen parent is the unpatented variety referred to as *Chamelaucium uncinatum* 'Z-10'. The new variety was discovered in March 2020 by the inventor in a group of seedlings resulting from previously mentioned crossing, in a commercial nursery in Kfar Hess, Israel.

Asexual reproduction of the new cultivar has been performed by terminal vegetative cuttings. This was first performed in June of 2020 at a commercial nursery in Kfar Hess, Israel and has shown that the unique features of this cultivar are stable and reproduced true to type in at least 5 successive generations.

SUMMARY OF THE INVENTION

The cultivar 'DUAL STAR' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DUAL STAR'. These characteristics in combination distinguish 'DUAL STAR' as a new and distinct *Chamelaucium* cultivar:

1. Large flower size.
2. Long internodes.
3. Winter blooming.
4. Flattened bud shape.
5. Large flower bud size.

PARENT COMPARISONS

Plants of the new cultivar 'DUAL STAR' are similar to plants of the seed parent in most horticultural characteristics, however, plants of the new cultivar 'DUAL STAR' differ in the following:

1. Flower size of the new variety is larger than the flower size of the seed parent.
2. Internodes of the new variety are longer than the internodes of the seed parent.
3. The new variety blooms in late winter, while the seed parent blooms in spring.

Plants of the new cultivar 'DUAL STAR' are similar to plants of the pollen parent in most horticultural characteristics, however, plants of the new cultivar 'DUAL STAR' differ in the following:

1. Flower size of the new variety is smaller than the flower size of the pollen parent.
2. Buds of the new variety are smaller than buds of the pollen parent.
3. The new variety blooms in late winter, while the pollen parent blooms in early winter.
4. Buds of the new variety are flattened, while buds of the pollen parent are round.

COMMERCIAL COMPARISON

Plants of the new cultivar 'DUAL STAR' are similar to plants of *Chamelaucium* 'Moon', U.S. Plant Pat. No. 36,174 in most horticultural characteristics, however, plants of the new cultivar 'DUAL STAR' differ in the following:

1. Bud shape: 'Dual Star' has a bud shape which is a flattened sphere; bud shape of 'Moon' is round.
2. Bud color: 'Dual Star' has a greyed-red flower bud; 'Moon' has a white flower bud.
3. Flower color: 'Dual Star' has a purple flower; 'Moon' has a white flower.

BRIEF DESCRIPTION OF THE PHOTOGRAPHS

The accompanying photograph in FIG. 1 illustrates in full color a close up of typical flowers and foliage of 'DUAL STAR' on a mature stem at approximately 1 year of age.

Figure 2:
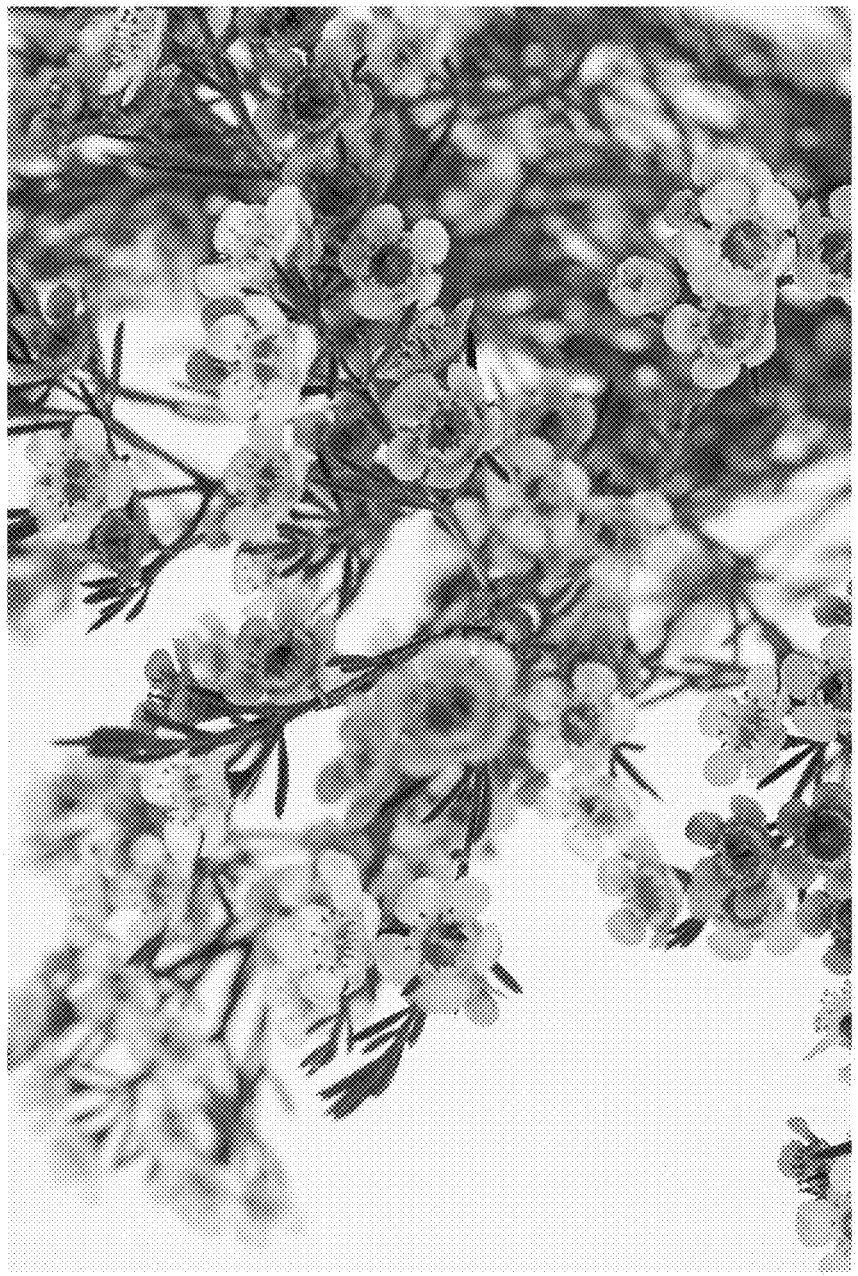

FIG. 2 illustrates a closer view of the flowers.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DUAL STAR' plants grown outdoors in Kfar Hess, Israel. The growing temperature ranged from 15° C. to 35° C. during the day and from −2° C. to 35° C. during the night. General light conditions are bright, normal sunlight. Measurements and numerical values represent averages of typical plant types.

Botanical classification: *Chamelaucium uncinatum* 'DUAL STAR'.

PROPAGATION

Time to produce a rooted plantlet: 30 to 60 days at approximately 24° C.

Root description: Split root.

PLANT

Age of plant described: About 2 months old from a rooted cutting.

Height: 135 cm to top of foliage; 133 cm to top of flowers.

Plant spread: 120 cm.

Branching characteristics:

Quantity of primary lateral branches: 100 to 120.

Characteristics of primary lateral branches:

*Length.*—Average range 60 to 130 cm.

*Diameter.*—0.45 cm, measured at 50 cm from top.

*Color.*—Near RHS Greyed-Green 197A.

*Texture.*—Smooth.

*Strength.*—Medium.

Internode length: 2 to 14 cm, section of top 5-30 cm.

FOLIAGE

Leaf:

*Arrangement.*—Opposite.

*Quantity.*—Approximately 6 leaves in the 5-10 cm section from the top of the branch.

*Length.*—2.2 cm.

*Width.*—1.1 mm.

*Shape.*—Needle.

*Apex.*—Acute.

*Base.*—Truncate.

*Margin.*—Smooth.

*Texture.*—Glabrous all surfaces.

*Aspect.*—Straight, occurring at an acute angle.

*Color.*—Young foliage, upper side: RHS Green 137A. Young foliage, under side: RHS Green 137A. Mature foliage, upper side: RHS Green 136A. Mature foliage, under side: RHS Green 136A.

*Venation.*—Indistinguishable from foliage.

*Petiole.*—Not present.

FLOWER

Natural flowering season: Winter.

Typical flowering stems harvested per plant: 100 to 120 during the course of the season.

Vase life of flowers: Two weeks.

Individual flower type: Single, rotate, 5 petals, about 1.6 cm in diameter.

Rate of flower opening: About 50 to 60 days from bud to fully opened flower.

Persistence: Self-cleaning.

Bud:

*Shape.*—Flattened sphere.

*Length.*—0.55 cm.

*Diameter.*—0.35 to 0.36 cm.

*Color.*—RHS Greyed-Red 179A.

Flower size:

*Diameter.*—1.6 cm.

*Length.*—0.8 cm.

Corolla:

*Petals.*—Arrangement: Rotate, non-overlapping. Length: 0.45 cm. Diameter: 0.6 cm. Quantity: 5. Texture: Smooth both surfaces. Apex: Blunt rounded. Base: Fused.

*Color.*—When opening: Upper surface: RHS White 155C. Lower surface: RHS White 155C. Fully opened: Upper surface: RHS Purple-Pink 73A. Lower surface: RHS Purple-Pink 73A. Aging: Upper surface: RHS Purple-Red 71A. Lower surface: RHS Purple-Red 71A.

Interior corolla/tube:

*Diameter.*—0.68 cm.

*Length.*—0.27 cm.

*Color.*—When opening: Upper surface: RHS Yellow-Green 146C. Lower surface: RHS Yellow 13B. Fully opened: Upper surface: RHS Yellow-Green 146C. Lower surface: RHS Orange-Yellow 163A. Aging: Upper surface: RHS Yellow-Green 146C. Lower surface: RHS Red 41B.

Calyx/sepals:

*Quantity per flower.*—5.

*Shape.*—Round.

*Length.*—0.35 cm.

*Width.*—0.35 cm.

*Margin.*—Smooth.

*Texture.*—Smooth both surfaces.

*Color.*—RHS Yellow-Green 144A.

Peduncle: Peduncle consists of the plant stem.

Pedicel:

*Length.*—0.9 cm.

*Diameter.*—0.07 cm.

*Color.*—RHS Green 137C.

Fragrance: None.

REPRODUCTIVE ORGANS

Stamens:

*Number.*—10.

*Filament length.*—1.8 mm.

Anthers:

*Shape.*—Ovate.

*Length.*—0.5 mm.

*Color.*—RHS Orange 22A.

*Pollen.*—Not observed.

Pistil:

*Number.*—1.

*Length.*—0.5 cm.

*Style Length.*—0.45 cm.

*Style color.*—RHS Purple-Pink 63B.

*Stigma.*—Shape: Round. Color: RHS Yellow 18C.

OTHER CHARACTERISTICS

Seeds and fruits: Single flower produces one fruit. When the fruit is fertile, it will produce one seed. Fruit and seeds are too small for accurate measurement of characteristics.

Disease/pest resistance: Neither resistance nor susceptibility to the normal diseases and pests of *Chamelaucium* have been observed to date.

Temperature tolerance: From −2° C. to 35° C.

What is claimed is:

1. A new and distinct cultivar of *Chamelaucium* plant named 'DUAL STAR' as herein illustrated and described.

* * * * *